(12) United States Patent
Schmidt et al.

(10) Patent No.: US 11,547,633 B2
(45) Date of Patent: Jan. 10, 2023

(54) DOSING SYRINGE

(71) Applicant: OBRIST CLOSURES SWITZERLAND GMBH, Reinach (CH)

(72) Inventors: Patrick Schmidt, Zell-Kaimt (DE); Klaus Thanisch, Bullay (DE)

(73) Assignee: OBRIST CLOSURES SWITZERLAND GMBH, Reinach (CH)

(*) Notice: Subject to any disclaimer, the term of this patent is extended or adjusted under 35 U.S.C. 154(b) by 370 days.

(21) Appl. No.: 16/609,816

(22) PCT Filed: May 4, 2018

(86) PCT No.: PCT/EP2018/061621
§ 371 (c)(1),
(2) Date: Oct. 31, 2019

(87) PCT Pub. No.: WO2018/202902
PCT Pub. Date: Nov. 8, 2018

(65) Prior Publication Data
US 2020/0054528 A1 Feb. 20, 2020

(30) Foreign Application Priority Data
May 4, 2017 (GB) ..................... 1707110

(51) Int. Cl.
*A61J 7/00* (2006.01)
*A61M 5/315* (2006.01)

(52) U.S. Cl.
CPC ........ *A61J 7/0053* (2013.01); *A61M 5/31535* (2013.01); *A61M 5/31536* (2013.01); *A61M 5/31595* (2013.01); *A61M 2005/3154* (2013.01)

(58) Field of Classification Search
CPC .......... A61J 7/0053; A61M 2005/3154; A61M 5/31536; A61M 5/31535; A61M 5/315;
(Continued)

(56) References Cited

U.S. PATENT DOCUMENTS 4,750,373 A * 6/1988 Shapiro ................. B01L 3/0234
73/864.18
4,946,441 A 8/1990 Laderoute
(Continued)

FOREIGN PATENT DOCUMENTS

CA 2214468 A1 9/1997
FR 2536285 A1 5/1984
(Continued)

OTHER PUBLICATIONS

International Search Report for Great Britain Application No. GB1707110.1, dated Oct. 31, 2017.
(Continued)

*Primary Examiner* — Kevin C Sirmons
*Assistant Examiner* — Alexandra Lalonde
(74) *Attorney, Agent, or Firm* — Thomas|Horstemeyer, LLP

(57) ABSTRACT

A dosing syringe comprising a barrel and a piston is provided. The piston is slidably receivable in the barrel and can move within the barrel from a maximum inserted position to a withdrawn position to draw a dose of a product into the barrel. The syringe comprises means for pre-setting the withdrawn position, which defines a maximum dose which can be drawn into the barrel.

18 Claims, 7 Drawing Sheets

(58) Field of Classification Search
CPC ...... A61M 5/31; A61M 5/178; A61M 5/3156;
A61M 5/31548; A61M 5/31545; A61M
5/31533; A61M 5/31563; A61M 5/31556;
A61M 5/3148; A61M 5/3155; A61M
5/31595; A61M 5/31501
See application file for complete search history.

(56) References Cited

U.S. PATENT DOCUMENTS

| | | | | |
|---|---|---|---|---|
| 2008/0132852 | A1* | 6/2008 | Kleyhan | A61M 5/31595 |
| | | | | 604/210 |
| 2009/0177156 | A1* | 7/2009 | MacLean | A61M 5/3155 |
| | | | | 604/135 |
| 2012/0203184 | A1 | 8/2012 | Selz et al. | |
| 2013/0204130 | A1 | 8/2013 | McArthur et al. | |
| 2014/0336591 | A1 | 11/2014 | Skaper et al. | |
| 2015/0119810 | A1 | 4/2015 | Jakob et al. | |
| 2016/0166772 | A1* | 6/2016 | Mirzazadeh | A61M 5/3157 |
| | | | | 604/222 |

FOREIGN PATENT DOCUMENTS

| | | | |
|---|---|---|---|
| GB | 1230522 | A | 5/1971 |
| WO | 2014162551 | A1 | 10/2014 |
| WO | 2017062304 | A1 | 4/2017 |

OTHER PUBLICATIONS

Written Opinion for International Application No. PCT/EP2018/061621, dated Aug. 1, 2018.

\* cited by examiner

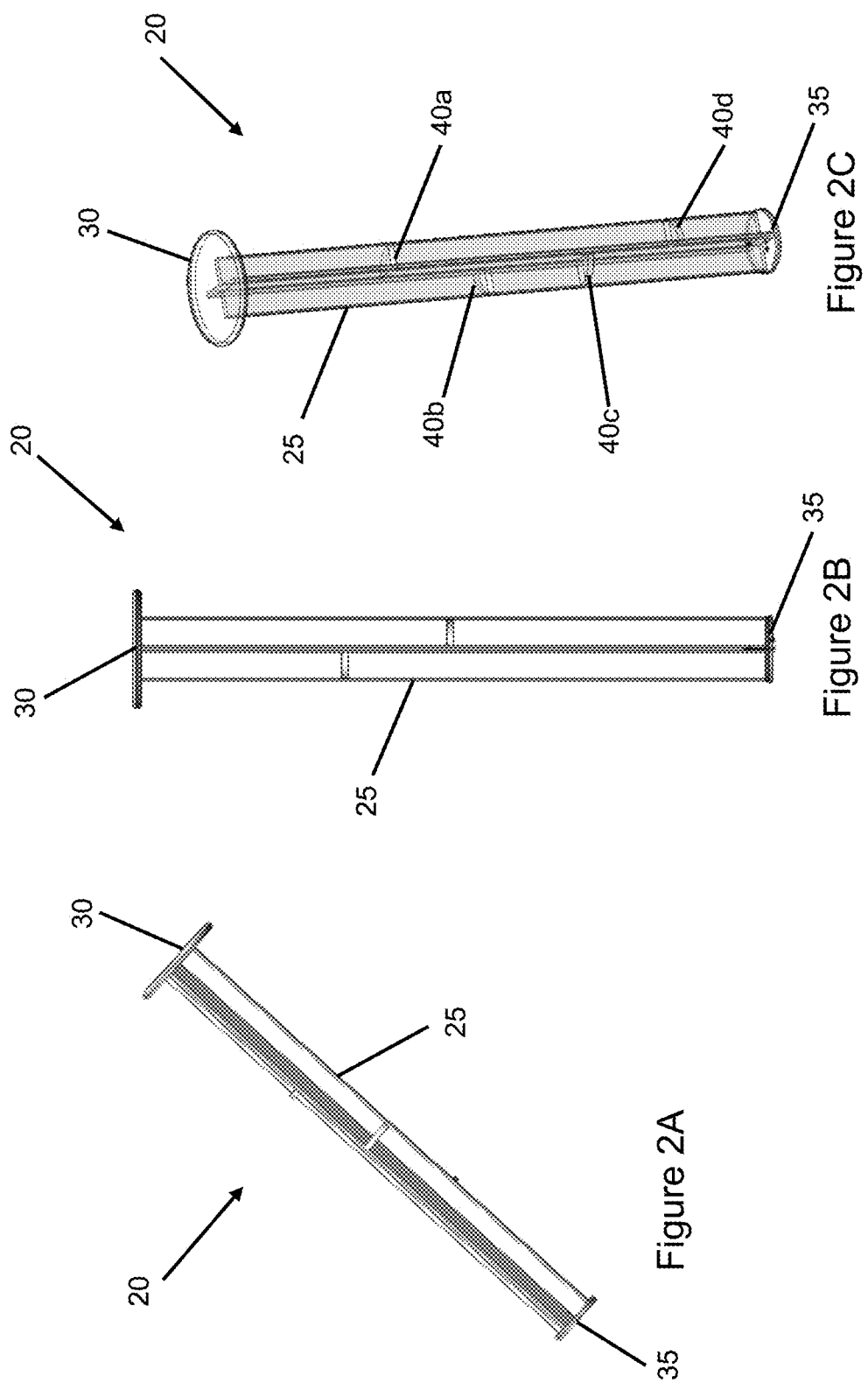

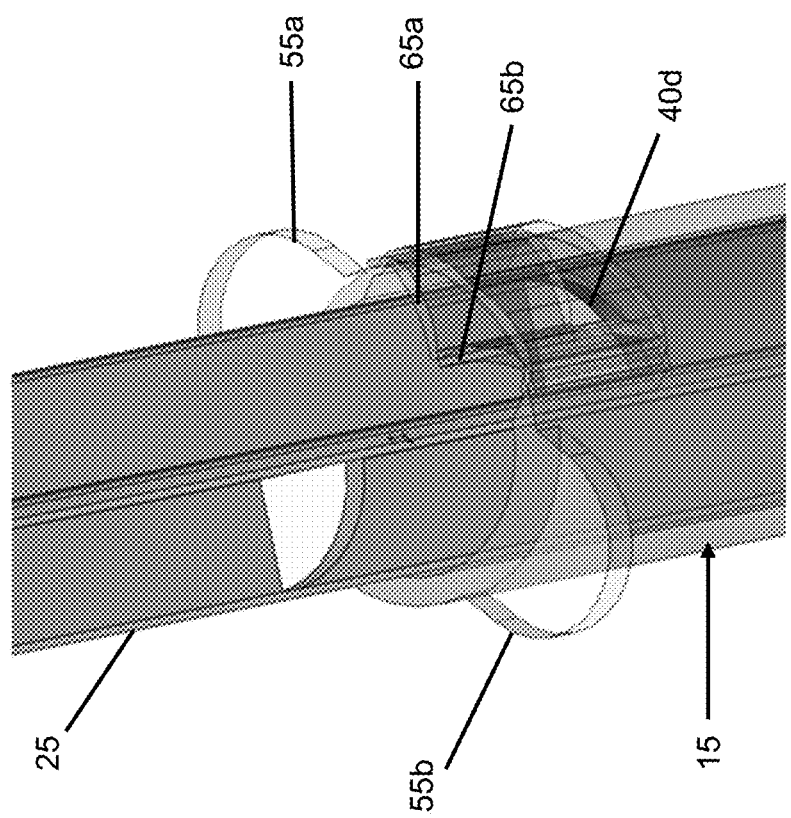

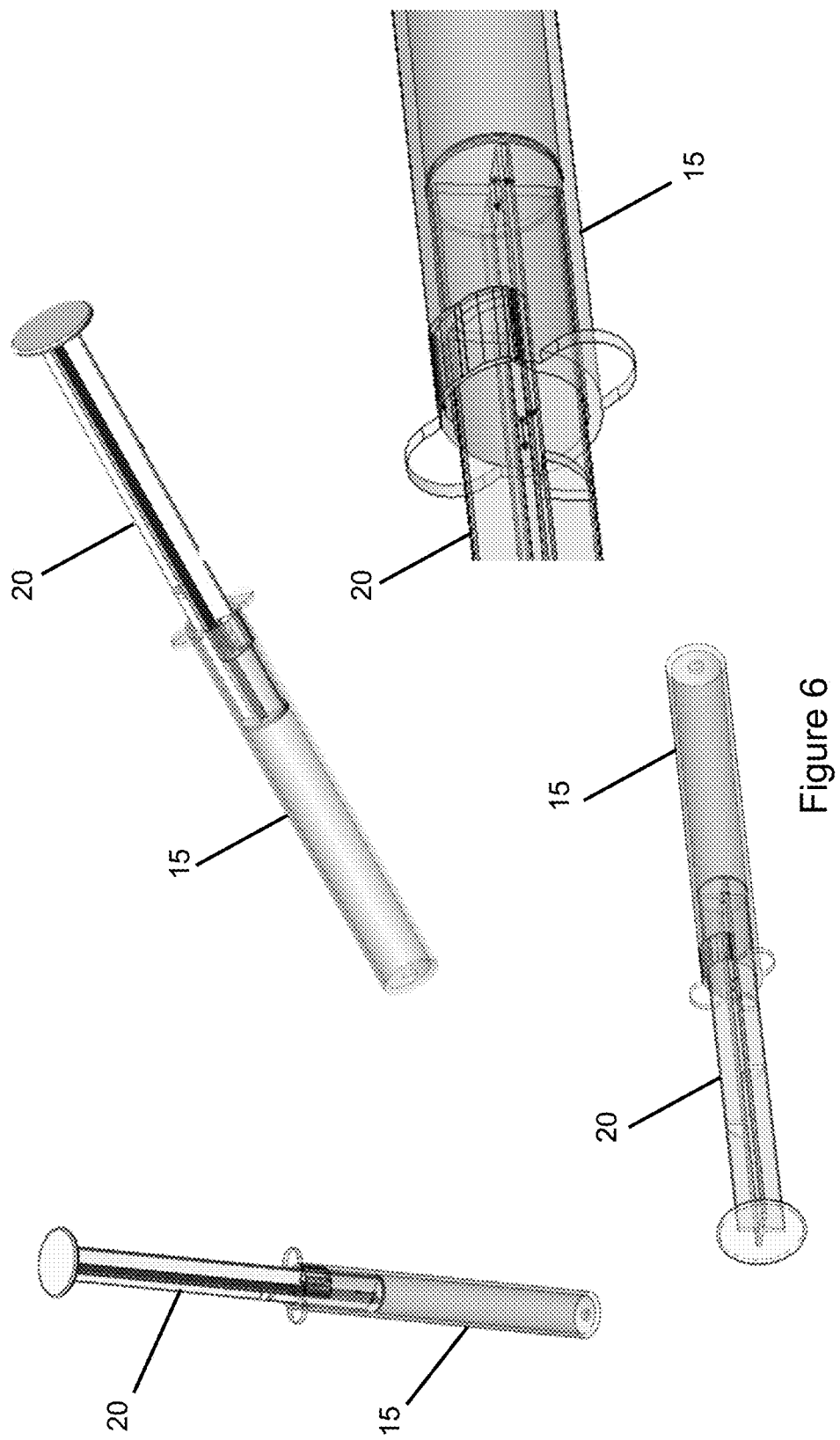

DOSING SYRINGE

CROSS-REFERENCE TO RELATED APPLICATIONS

This application is the 35 U.S.C. § 371 national stage of PCT application having serial number PCT/EP2018/061621, filed on May 4, 2018. This application also claims priority to GB application entitled "DOSING SYRINGE," having serial number 1707110.1 filed on May 4, 2017, which are entirely incorporated herein by reference.

The present invention relates generally to a syringe and particularly to a dosing syringe for delivering a required dose of a product, for example a flowable product.

BACKGROUND

A syringe is a reciprocating pump consisting of a sliding piston/plunger that fits tightly in a barrel/tube. The plunger can be pulled and pushed inside the cylindrical tube, or barrel, letting the syringe draw in or expel a liquid or gas through an orifice at the open end of the tube. Pressure is used to operate a syringe. Plastics and disposable syringes are often used to administer medications.

In normal operation, first the plunger is in a bottom position (normally maximally inserted into the barrel). Then the end of the barrel (and/or nozzle, needle or the like extending therefrom) is dipped into the fluid and the plunger is pulled back to or towards a top position, thus pulling the fluid inside the tube. When the plunger is pulled back a partial vacuum is created in the tube resulting in pressure difference. Pressure inside the barrel is lower than atmospheric pressure hence fluid enters the tube to establish pressure equilibrium. When the plunger is pushed back to or towards the bottom, it exerts pressure on the fluid to cause it to exit the syringe.

Currently, syringes are in use wherein the amount to be taken has to be adjusted by the user. However, there is a huge failure rate with the dosing, for which reason users very often use the wrong amount of syrup (didn't read the instructions, not using the right amount according to the weight of a baby, handling problems etc.).

The present invention seeks to address problems with known syringes.

BRIEF DESCRIPTION OF THE DRAWINGS

The present invention is more particularly described, by way of example, with reference to the accompanying drawings, in which:

FIGS. 2A to 2C are views of a plunger/piston of the dosing syringe of FIG. 1;

FIG. 5 is a detailed view of a barrel and plunger/piston of the dosing syringe of FIG. 1;

FIG. 6 are further views of a barrel and plunger/piston of the dosing syringe of FIG. 1;

DETAILED DESCRIPTION

Figure 1:
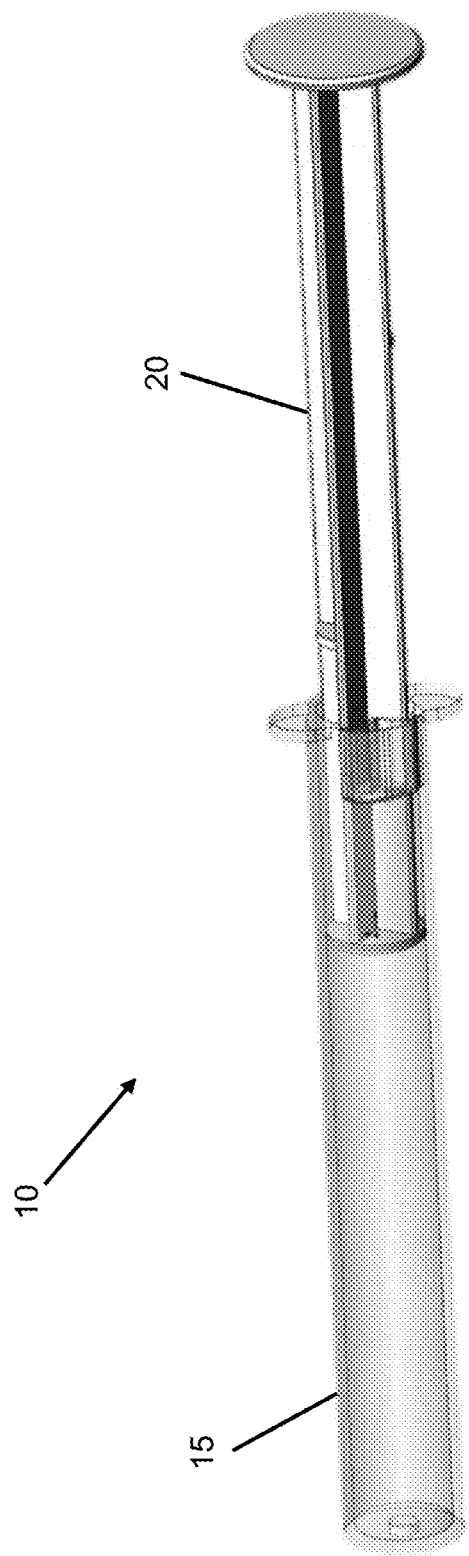
FIG. 1 is a perspective view of a dosing syringe in accordance with the present invention.

According to the present invention there is provided a dosing syringe comprising a barrel and a piston, the piston is slidably receivable in the barrel and can move within the barrel from a maximum inserted position to a withdrawn position to draw a dose of product into the barrel, the syringe comprises means for pre-setting the withdrawn position whereby to define the maximum dose which can be drawn into the barrel.

In some embodiments the syringe can be adjusted to provide a plurality of different withdrawn positions.

In some respects the invention may be based on a principle of changing the effective length of the piston.

In some embodiments the syringe is provided with a plurality of pre-settable stopping ribs.

In some embodiments the syringe is configured to help prevent mis-dosing.

In some embodiments a plurality of compartments are formed in the syringe.

The barrel may be generally cylindrical.

Adjusting between withdrawn positions may be determined by relative rotational orientation between the barrel and the piston.

The barrel may include a blocking projection and the piston may include one or more cooperating projections which together define one or more maximum withdrawn positions of the piston.

The or each projection on the piston comprises a rib, for example a transverse rib extending from a central piston stem. The piston stem may, for example, have a generally cruciform section and the ribs may be generally quadrant-shaped.

The piston/plunger may have a generally disc-shape flange at either end. One of the flanges forms a seal within the bore/lumen of the barrel; the other flange is used to pull/push the piston into/out of the barrel.

The barrel may have a barrel flange at one end thereof.

In some embodiments the blocking projection of the barrel can be reversibly moved between an unblocking position to a blocking position. In other embodiments the blocking projection of the barrel is irreversibly movable from an unblocking position to a blocking position.

The barrel may have a dosing end with a flat nose.

In some embodiments the syringe allows the amount to be dosed to be pre-set by using some blocking ribs located within the piston which interacts with the recess on the upper end of the barrel. The location of the ribs correlates to the amount to be dosed; i.e. the lowest rib allows 2.5 ml to be withdrawn out of a bottle before the rib at the piston will be blocked by the upper end of the barrel. The recess at the barrel is deformable and is pressed into the barrel interior. The piston is divided into three compartments by longitudinal ribs (standard syringe). Within each of these three compartments a traverse rib is present. These ribs indicate how far the piston can move upwards. The deformable region once pressed into the barrel interior will—depending on the orientation of the piston—allow to dose, for example, 2.5 ml (lowest blocking rib), 5 ml (middle blocking rib) or 7 ml (highest blocking rib). This snap in deformable region may be reversible so that also another dosage amount can be chosen.

The present invention also provides a dosing syringe for delivering a required dose of pharmaceutical syrup product, the syringe having a plurality of different pre-settable doses, the doses being determined by the extent to which the piston can be withdrawn from the barrel, a maximally withdrawn end position of the piston being determined by relative rotational orientation between the piston and the barrel.

The present invention also provides a dosing syringe comprising a barrel and a piston, the syringe allows pre-setting of the amount to be dosed by using blocking ribs located within the piston which interact with a recess on the upper end of the barrel.

Increments/differences between different doses may be in the range 1 ml to 5 ml.

In some embodiments the dosing amounts may be one or more selected from 2.5 ml, 5 ml, 7.5 ml and 10 ml.

In some aspects and embodiments three, four or five different doses can be provided; for example: 2.5 ml; 5 ml; or 7.5 ml.

In some embodiments the plunger can be locked in a maximally or near maximally inserted position. This could be used, for example, to prevent any dispensing at all.

A further aspect provides a dosing syringe comprising a tube and a plunger, the plunger is slidably receivable in the tube and can move within the tube from an inserted position to a withdrawn position to draw a dose of product into the tube, the syringe comprises means for pre-setting the withdrawn position whereby to define the maximum dose which can be drawn into the tube.

The present invention also provides a pharmaceutical syrup dispensing syringe comprising a syringe as described herein.

The present invention also provides a syringe as described herein in combination with a container of product to be dispensed.

Particular and preferred aspects and embodiments of the present invention are set out in the accompanying independent and dependent claims. Features of the dependent claims may be combined with the features of the independent claims as appropriate, and in combination other than those explicitly set out in the claims.

The example embodiments are described in sufficient detail to enable those of ordinary skill in the art to embody and implement the systems and processes herein described. It is important to understand that embodiments can be provided in many alternate forms and should not be construed as limited to the examples set forth herein.

Accordingly, while embodiments can be modified in various ways and take on various alternative forms, specific embodiments thereof are shown in the drawings and described in detail below as examples. There is no intent to limit to the particular forms disclosed. On the contrary, all modifications, equivalents, and alternatives falling within the scope of the appended claims should be included. Elements of the example embodiments are consistently denoted by the same reference numerals throughout the drawings and detailed description where appropriate.

Unless otherwise defined, all terms (including technical and scientific terms) used herein are to be interpreted as is customary in the art. It will be further understood that terms in common usage should also be interpreted as is customary in the relevant art and not in an idealised or overly formal sense unless expressly so defined herein.

The figures are not necessary drawn to scale, and in some instances the drawings may have been exaggerated or simplified for illustrative purposes only. One of ordinary skill in the art will appreciate the many possible applications and variations of the present invention based on the following examples of possible embodiments of the present invention.

Referring first to FIG. 1 there is shown a dispensing syringe generally indicated 10.

The syringe 10 comprises a barrel 15 and a cooperating plunger/piston 20 which is adapted to slide within the internal bore of the barrel.

Referring now also to FIGS. 2A-2C the piston 20 comprises an elongate generally cruciform-section central stem 25, which in some senses divides the piston into four quadrants, each bounded by two legs of the stem.

At one end of the stem is a disc-shape piston flange 30. At the other end of the stem is a sealing flange 35 which slidingly seals on the interior surface of the barrel.

As shown best in FIG. 2C, four quadrant-shape blocking ribs 40a, 40b, 40c, 40d are provided; each rib extends between two legs of the stem. There is only one rib in each quadrant of the stem and each of the ribs is at a different point along the length of the stem.

Figure 3B:
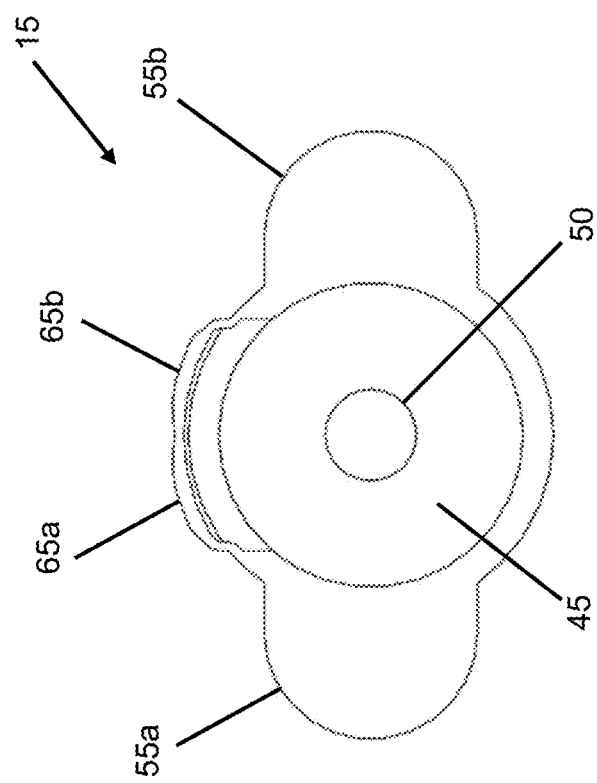
FIGS. 3A and 3B are views of a barrel of the dosing syringe of FIG. 1.
Figure 3A:
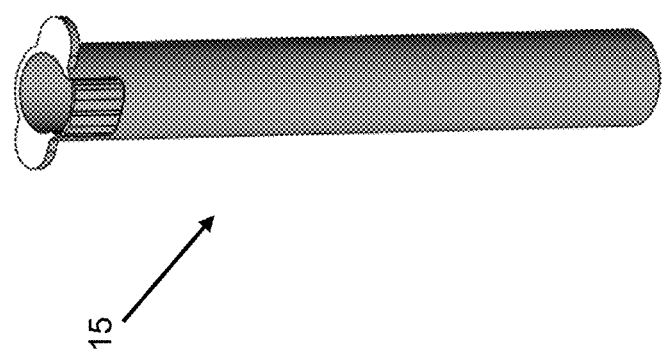

Referring now to also to FIGS. 3A (perspective view) and 3B (plan view) the barrel 15 is a generally cylindrical tube. One end of the barrel is a dosing end and terminates with a flat nose; that end being partially closed by a disc shape end plate 45 with a central dispensing orifice 50. The other end of the barrel is open (and receives the piston in use) and has an opposing pair of external flanges 55a, 55b useful for helping to depress the piston.

At one side of the piston-receiving end of the barrel, in between the flanges, is a deformable region 60.

Figure 4B:
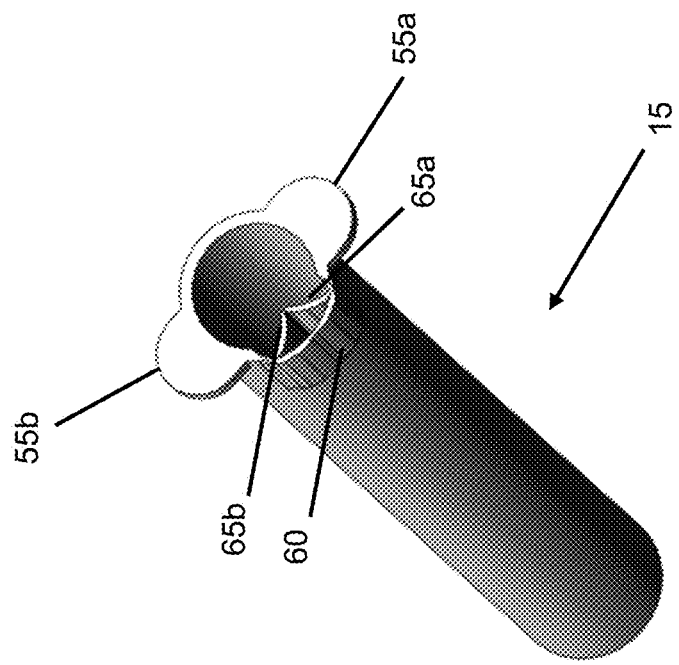
FIGS. 4A and 4B are further views of a barrel of the dosing syringe of FIG. 1.
Figure 4A:
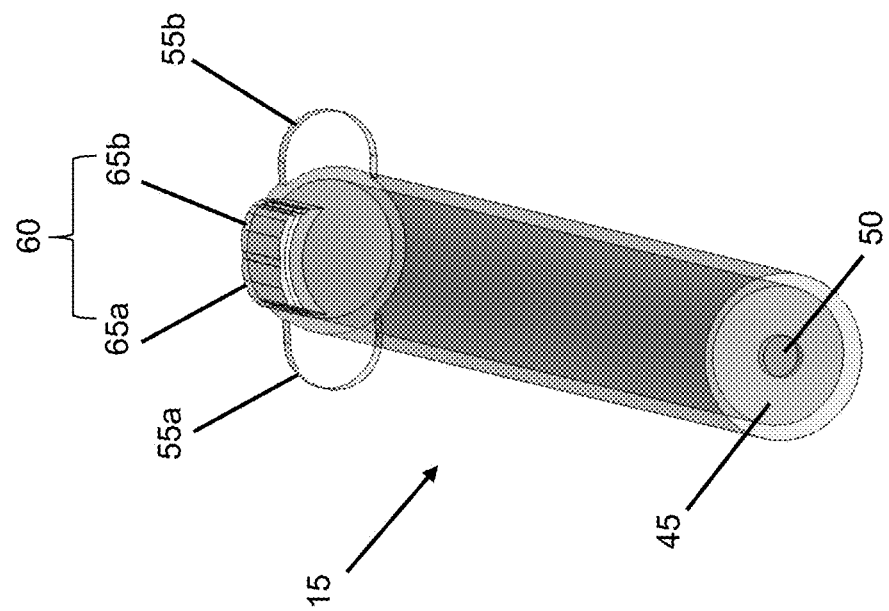

The region 60 comprises a pair of arcuate flaps 65a, 65b which are joined together and can be moved radially inwards from a non-blocking position shown in FIG. 4A to a blocking position shown in FIG. 4B in which they extend into the lumen of the barrel. In this embodiment each flap is hinged to the barrel wall and also hinged to each other. Movement of the flaps can be reversed.

As illustrated in FIG. 5, the piston 20 is inserted into the barrel 15. If the flaps are in the non-blocking position the piston can freely move up and down in the barrel (and could be completely withdrawn).

Figure 7:
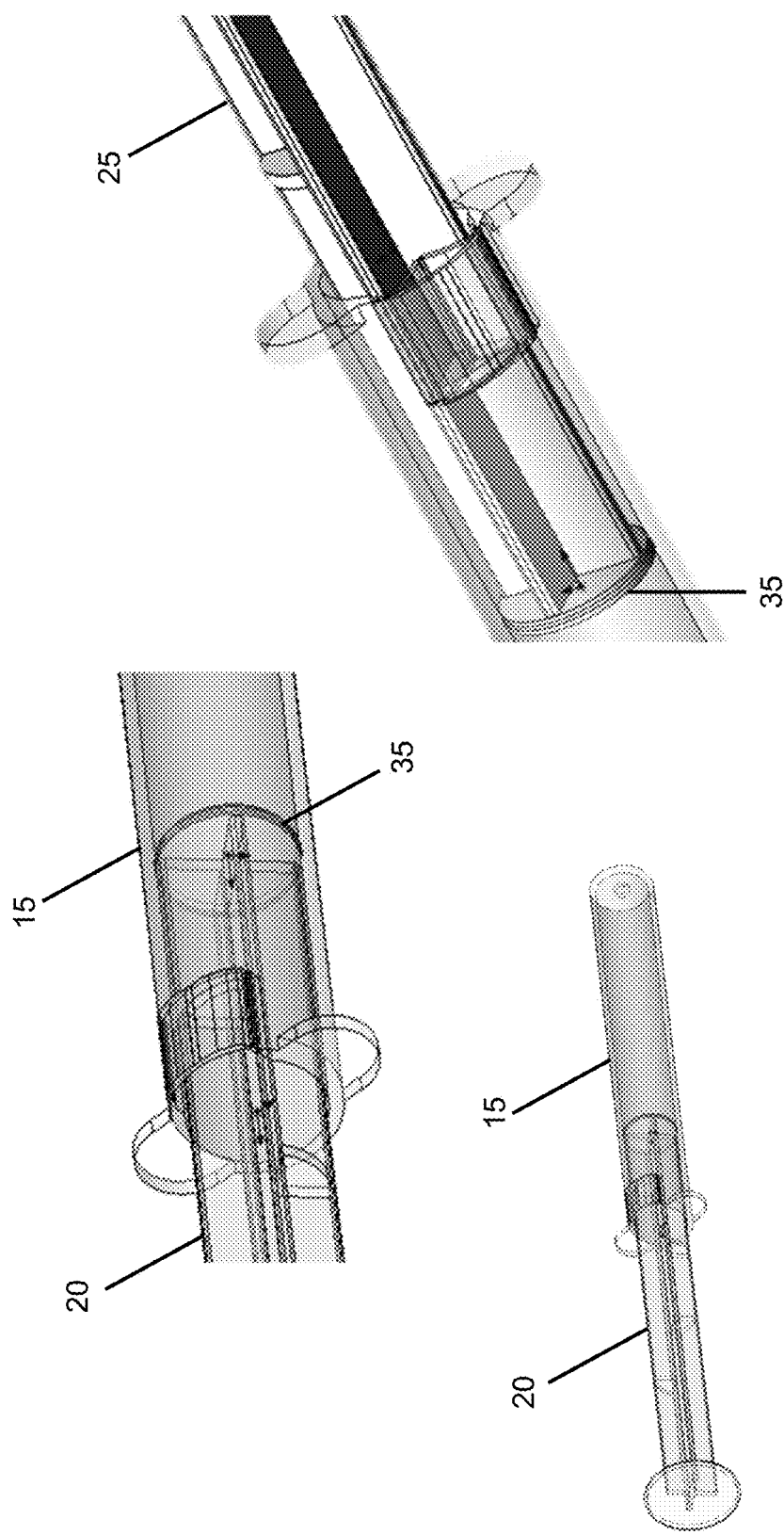
FIG. 7 are further detailed views of a barrel and plunger/piston of the dosing syringe of FIG. 1.

However, if the flaps are pressed inwards this will prevent the piston from rotating within the barrel, thus setting the relative rotational orientation. This also means that one of the four quadrants of the stem is now in line with the flaps. Consequently this means that the blocking rib within that quadrant cannot pass over the flaps. In turn this thereby sets the maximum amount the piston can be withdrawn from the barrel in use. Because the four ribs are all at different points along the stem, by pre-selecting the stem quadrant into which the flaps are moved it is possible to determine the maximum amount the piston can be withdrawn and hence how much product can be drawn into the barrel. FIG. 5 shows the rib 40d being selected and abutting against the undersides of the flaps to prevent further piston withdrawal. Further views of this selected end position are shown in FIGS. 6 and 7. It may also be possible to use the syringe without the flaps engaged and withdraw the piston so that it is just below the barrel flanges. In total this would give five different doses (only four of which needing to use the flaps).

In a further embodiment a syringe allows the amount to be dosed to be pre-set by using some blocking ribs located within the piston which interacts with the recess on the upper end of the barrel. The location of the ribs correlates to the amount to be dosed. A lowest rib allows 2.5 ml to be withdrawn out of a bottle before the rib at the piston will be blocked by the upper end of the barrel. The recess at the barrel is deformable and is pressed into the barrel interior. The piston is divided into three compartments by longitudinal ribs (standard syringe). Within each of these three compartments a traverse rib is present. These ribs indicate how far the piston can move upwards. The deformable region once pressed into the barrel interior will—depending on the orientation of the piston—allow to dose 2.5 ml (lowest blocking rib), 5 ml (middle blocking rib) or 7 ml (highest blocking rib). This snap in deformable region may be reversible so that also another dosage amount can be chosen.

In some aspects and embodiments the syringe is intended to be used for pharmaceutical syrups.

Although illustrative embodiments of the invention have been disclosed in detail herein, with reference to the accompanying drawings, it is understood that the invention is not limited to the precise embodiments shown and that various changes and modifications can be effected therein by one skilled in the art without departing from the scope of the invention.

The invention claimed is:

1. A dosing syringe comprising a barrel and a piston, wherein the piston is slidably receivable in the barrel and can move within the barrel from a maximum inserted position to at least one withdrawn position to draw a dose of a product into the barrel, and wherein the syringe comprises means for pre-setting each of the at least one withdrawn positions whereby to define a maximum dose which can be drawn into the barrel;
wherein the means for pre-setting each of the at least one withdrawn positions comprises:
a deformable region of the barrel comprising a deformable pair of arcuate flaps and one or more cooperating projections of the piston which together define one or more maximum withdrawn positions of the piston,
and wherein the deformable pair of arcuate flaps are movable radially inwards relative to the barrel between an unblocking position and a blocking position in which the deformable pair of arcuate flaps extend into a lumen of the barrel and prevent the one or more cooperating projections of the piston from passing over the deformable pair of arcuate flaps.

2. The syringe as claimed in claim 1, in which the syringe can be adjusted to provide a plurality of different maximum withdrawn positions.

3. The dosing syringe according to claim 2, in which the one or more cooperating projections are blocking ribs, wherein a location of the blocking ribs correlates to an amount to be dosed, a lowest blocking rib allows a lowest amount to be withdrawn out of a bottle before the lowest blocking rib at the piston will be blocked by an upper end of the barrel, a recess at the upper end of the barrel is deformable and is configurable to be pressed into an interior of the barrel, the piston is divided into three compartments by longitudinal ribs, within each of these compartments a blocking rib of the blocking ribs is present, wherein each blocking rib indicates how far the piston can move upwards, the deformable recess once pressed into the interior of the barrel will, depending on an orientation of the piston, allow to dose the lowest amount determined by the lowest blocking rib, a middle amount determined by a middle blocking rib or a highest amount determined by a highest blocking rib.

4. The dosing syringe according to claim 3, in which the deformable recess is reversible so that another dosage amount can be pre-set.

5. The dosing syringe according to claim 3, in which the lowest amount is approximately 2.5 ml, the middle amount is approximately 5 ml and the highest amount is approximately 7 ml.

6. The syringe as claimed in claim 1, in which the barrel is generally cylindrical.

7. The syringe as claimed in claim 1, in which adjusting between withdrawn positions is determined by relative rotational orientation between the barrel and the piston.

8. The syringe as claimed in claim 1, in which the one or more cooperating projections comprises a rib.

9. The syringe as claimed in claim 1, in which the deformable pair of arcuate flaps of the barrel can be reversibly moved between the unblocking position to the blocking position.

10. The syringe as claimed in claim 1, in which the deformable pair of arcuate flaps of the barrel is irreversibly movable from the unblocking position to the blocking position.

11. The syringe as claimed in claim 1, in which the barrel has a dosing end with a flat nose.

12. The syringe as claimed in claim 1, in which there are two, three, four or five different possible fixed doses.

13. The syringe as claimed in claim 1, in which the syringe allows the maximum dose to be pre-set by using the one or more cooperating projections which are blocking ribs located within the piston which interact with a recess on an upper end of the barrel, the location of the blocking ribs correlates to the maximum dose which is pre-set, the recess on the barrel is a deformable recess and can be pressed into an interior of the barrel, the piston is divided into multiple compartments by longitudinal ribs, within each of the compartments at least one blocking rib is present, the blocking ribs indicate how far the piston can move upwards, the deformable recess once pressed into the interior of the barrel will, depending on an orientation of the piston, control the maximum dose.

14. The dosing syringe as claimed in claim 1, in which increments between different doses are in a range of 1 ml to 5 ml.

15. The syringe as claimed in claim 1, in which the maximum dose is one or more selected from 2.5 ml, 5 ml, 7.5 ml and 10 ml.

16. A dosing syringe for delivering a required dose of a pharmaceutical syrup product, the syringe having a plurality of different pre-settable doses, the plurality of pre-settable doses being determined by an extent to which a piston can be withdrawn from a barrel, a maximally withdrawn end position of the piston being determined by relative rotational orientation between the piston and the barrel,
wherein the barrel includes a deformable region comprising a deformable pair of arcuate flaps and the piston includes one or more cooperating projections which together define one or more maximum withdrawn positions of the piston,
and wherein the deformable pair of arcuate flaps are movable radially inwards relative to the barrel between an unblocking position and a blocking position in which the deformable pair of arcuate flaps extend into a lumen of the barrel and prevent the one or more cooperating projections of the piston from passing over the deformable pair of arcuate flaps.

17. A dispensing syringe comprising a barrel and a cooperating plunger/piston which is adapted to slide within an internal bore of the barrel, the cooperating plunger/piston comprises an elongate generally cruciform-section central stem, which divides the cooperating plunger/piston into four quadrants, each bounded by two legs of the stem, at one end of the stem is a disc-shape piston flange, at the other end of the stem is a sealing flange which slidingly seals on an interior surface of the barrel, four quadrant-shape blocking ribs are provided, each blocking rib extends between the two legs of the stem, there is only one blocking rib in each quadrant of the stem and each of the blocking ribs is at a different point along a length of the stem, the barrel is a generally cylindrical tube, one end of the barrel is a dosing end and terminates with a flat nose, the dosing end being partially closed by a disc shape end plate with a central dispensing orifice, the other end of the barrel is open and receives the cooperating plunger/piston in use, and has an opposing pair of external flanges useful for helping to depress the cooperating plunger/piston, at one side of the end of the barrel that is open and receives the cooperating plunger/piston, in between the opposing pair of external flanges, is a deformable region, the deformable region comprises a pair of arcuate flaps which are joined together and can be moved radially inwards from a non-blocking position to a blocking position in which the pair of arcuate flaps extend into a lumen of the barrel, each flap is hinged to a barrel wall and also hinged to each other, movement of the flaps can be reversed, in use the cooperating plunger/piston is inserted into the barrel, if the flaps are in the non-blocking position the cooperating plunger/piston can freely move up and down in the barrel, and could be completely withdrawn, however, if the flaps are pressed inwards this will prevent the cooperating plunger/piston from rotating within the barrel, thus setting a relative rotational orientation, this also means that one of the four quadrants of the stem is now in line with the flaps, consequently this means that the blocking rib within a particular one of the four quadrants of the stem in line with the flaps cannot pass over the flaps, in turn this thereby sets a maximum amount the cooperating plunger/piston can be withdrawn from the barrel in use, because each of the four blocking ribs are at different points along the stem, by pre-selecting the quadrant of the stem into which the flaps are moved it is possible to determine the maximum amount the cooperating plunger/piston can be withdrawn and hence how much product can be drawn into the barrel.

18. The dispensing syringe according to claim 17, in which a dose can be delivered without the flaps engaged by withdrawal of the cooperating plunger/piston to a location above the blocking ribs and below a bottom surface of the opposing pair of barrel flanges, in total giving five different doses, only four of which are set by the flaps.

* * * * *